(12) United States Patent
Suh et al.

(10) Patent No.: US 10,881,431 B2
(45) Date of Patent: Jan. 5, 2021

(54) HAIR IMPLANTER WITH AUTOMATICALLY RETRACTING NEEDLE

(71) Applicants: Electronics and Telecommunications Research Institute, Daejeon (KR); Kyungpook National University Industry-Academic Cooperation Foundation, Daegu (KR)

(72) Inventors: Jung Wook Suh, Daegu (KR); Kyu Hyung Kim, Daegu (KR); Moon Kyu Kim, Daegu (KR); Jung Chui Kim, Daegu (KR); Tae Wuk Bae, Daegu (KR); Eun Chang Choi, Daegu (KR)

(73) Assignees: ELECTRONICS AND TELECOMMUNICATIONS RESEARCH INSTITUTE, Daejeon (KR); Kyungpook National University Industry-Academic Cooperation Foundation, Daegu (KR)

( * ) Notice: Subject to any disclaimer, the term of this patent is extended or adjusted under 35 U.S.C. 154(b) by 205 days.

(21) Appl. No.: 16/105,810

(22) Filed: Aug. 20, 2018

(65) Prior Publication Data
US 2019/0053827 A1    Feb. 21, 2019

(30) Foreign Application Priority Data

Aug. 18, 2017 (KR) .................. 10-2017-0104981
Jan. 11, 2018 (KR) .................. 10-2018-0003872

(51) Int. Cl.
*A61B 17/34* (2006.01)
*A61F 2/10* (2006.01)
*A61M 5/32* (2006.01)
*A61B 17/00* (2006.01)

(52) U.S. Cl.
CPC ............ *A61B 17/3468* (2013.01); *A61F 2/10* (2013.01); *A61M 5/3221* (2013.01); *A61M 5/3234* (2013.01); *A61B 2017/00398* (2013.01); *A61B 2017/00752* (2013.01)

(58) Field of Classification Search
None
See application file for complete search history.

(56) References Cited

U.S. PATENT DOCUMENTS

| 3,288,115 A | 11/1966 | Hechtle |
| 4,378,019 A * | 3/1983 | Yamada .................... A61F 2/10 606/187 |

(Continued)

FOREIGN PATENT DOCUMENTS

| JP | 10151134 A * | 6/1998 | ......... A61B 17/3468 |
| JP | 10211204 A * | 8/1998 | ......... A61B 17/3468 |

(Continued)

OTHER PUBLICATIONS

EPO/Google Machine Translation of JPH 10151134A (Year: 1998).*

*Primary Examiner* — Shaun L David

(57) ABSTRACT

The present disclosure relates to a hair implanter with an automatically retracting needle, and more specifically, to a hair implanter with an automatically retracting needle configured to automatically move a needle backward by a force of a spring when the needle is moved forward to a predetermined position to allow hair transplantation work to be smoothly performed.

14 Claims, 12 Drawing Sheets

(56) References Cited

U.S. PATENT DOCUMENTS

| | | | | |
|---|---|---|---|---|
| 5,439,475 A | * | 8/1995 | Bennett | A61B 17/3468 606/187 |
| 5,817,120 A | * | 10/1998 | Rassman | A61B 17/3468 606/187 |
| 6,461,369 B1 | * | 10/2002 | Kim | A61B 17/3468 606/187 |
| 2003/0097144 A1 | * | 5/2003 | Lee | A61B 17/3468 606/187 |
| 2004/0193203 A1 | * | 9/2004 | Pak | A61B 17/3468 606/187 |
| 2005/0096687 A1 | * | 5/2005 | Rassman | A61B 17/3468 606/187 |
| 2005/0187573 A1 | * | 8/2005 | Rassman | A61B 17/3468 606/187 |
| 2005/0203545 A1 | * | 9/2005 | Cole | A61B 17/32053 606/133 |
| 2011/0319921 A1 | * | 12/2011 | Giotis | A61B 17/32053 606/187 |
| 2013/0226214 A1 | * | 8/2013 | Okuda | A61B 17/3468 606/187 |
| 2014/0188150 A1 | * | 7/2014 | Oc | A61B 17/3468 606/187 |
| 2016/0120574 A1 | * | 5/2016 | Shiao | A61F 2/10 606/187 |
| 2016/0213400 A1 | * | 7/2016 | Oc | A61B 17/3468 |
| 2017/0020564 A1 | * | 1/2017 | Bae | A61B 17/3468 |
| 2017/0135713 A1 | | 5/2017 | Suh et al. | |
| 2018/0085143 A1 | * | 3/2018 | DeYarman | A61B 17/3417 |

FOREIGN PATENT DOCUMENTS

| | | | |
|---|---|---|---|
| JP | 10286257 A | * 10/1998 | A61B 17/3468 |
| JP | 11104138 A | * 4/1999 | A61B 17/3468 |
| KR | 20000065685 A | 11/2000 | |
| KR | 200368968 B1 | 12/2004 | |
| KR | 1020130014350 A | 2/2013 | |
| KR | 101600758 B | 3/2016 | |

* cited by examiner

HAIR IMPLANTER WITH AUTOMATICALLY RETRACTING NEEDLE

CROSS-REFERENCE TO RELATED APPLICATION

This application claims priority to and the benefit of Korean Patent Application Nos. 10-2017-0104981 and 10-2018-0003872, filed on Aug. 18, 2017 and Jan. 11, 2018, which are incorporated by reference for all purposes as if fully set forth herein.

BACKGROUND

1. Field of the Invention

The present disclosure relates to a hair implanter with an automatically retracting needle, and more specifically, to a hair implanter with an automatically retracting needle configured to automatically move a needle backward by a force of a spring when the needle is moved forward to a predetermined position to allow hair transplantation work to be smoothly performed.

2. Discussion of Related Art

In general, hair transplantation surgery using a strip method, which is mainly performed in Korea, may be performed through processes of anesthesia, a strip incision, sewing, a follicular units extraction, and hair transplantation using a hair implanter.

Here, the hair follicular unit extraction process includes a strip collection method and a follicular unit extraction (FUE) method.

The strip collection method extracts a strip in a patient's occiput in a long shape, stitches the occiput, and then separates the extracted strip into hair follicular units, while the FUE method is a non-incision method in which a thin punching machine is used to extract hair follicles directly from a scalp.

In addition, a method of hair transplantation may be divided into two types, which are a method using a manual hair implanter and a method using tweezers.

Further, a method in which a small slit is made in an implant area requiring hair transplantation, and, using tweezers, hair follicles (hair) are directly pushed into a hole made by the slit is mainly used in western countries.

Meanwhile, in the method using a manual hair implanter which is widely used in Korea, there is no need to provide a separate slit, and hair follicles are not pressed while being planted, so the method may be seen as a more advanced type of hair transplantation.

Next, a process of planting hair follicles using a hair implanter will be described below. The hair transplantation process using a hair implanter includes putting a hair follicle-loaded hair implanter needle into a scalp, pushing the hair follicle with a push rod and pulling the needle out of the scalp, whereby pulling out the needle completely leaves the hair follicle in the scalp.

In the process of pulling out the needle, an operator lifts a body of the hair implanter using remaining fingers while pushing a rear part of the hair implanter with an index finger.

Here, the rear part is maintained in a fixed state with a nozzle and the push rod, and the body is maintained in a fixed state with the needle.

However, the process of lifting the body of the hair implanter and pulling out the needle in a state in which the index finger is fixed requires repeated practice, and when a height of the index finger is not properly maintained in the process of pulling out the needle, a height of the push rod which pushes the hair follicle may be changed to cause the hair follicle to come out of the scalp or be inserted too deeply.

In addition, when the height of the hair follicle planted as described above is not proper, the scalp becomes uneven, and in the worst case, the planted hair follicle dies and hair does not come out.

SUMMARY OF THE INVENTION

The present disclosure is directed to a hair implanter with an automatically retracting needle capable of easily adjusting a height of a hair follicle to a height of a scalp in a hair transplantation process.

According to an aspect of the present disclosure, there is provided a hair implanter with an automatically retracting needle including a case which has a hollow shape and includes a mounting portion formed at one end thereof and a nozzle hole formed at the other end thereof; a fixing member which has a hollow shape, is coupled to the mounting portion of the case, and includes a fixing guide portion formed at one end thereof and a step portion formed at the other end thereof; a push member which operates forward and backward and includes one end provided with a needle supporting groove and disposed on the step portion of the fixing member and the other end disposed on the outside; a connection member disposed inside the fixing member and operating in conjunction with the operation of the push member; a moving member which is disposed inside the case, operates in conjunction with the operation of the push member, and includes a partition wall provided with a needle fixing hole formed at a center thereof and a moving guide portion formed at one end thereof; an elastic member including first and second springs disposed on both sides of the partition wall of the moving member, and configured to move the moving member in a direction of the nozzle hole when the push member is pressed and to move the push member and the moving member to an original position thereof when the moving member is moved in the pushing direction; and a hair transplantation needle which is fixed by the needle supporting groove of the push member and the needle fixing hole of the moving member.

An outer surface of the other end of the case, in which the nozzle hole is formed, is formed in a conical shape.

The fixing guide portion of the fixing member may include a first inclined surface positioned at an end thereof and formed to be inclined, a horizontal surface formed at an end of the first inclined surface, and a second inclined surface formed at an end of the horizontal surface, which are all disposed to be spaced apart from the fixing guide portion along a circumference of an edge of the fixing member.

The first inclined surface may be formed in multiple stages.

The connection member may include a supporting portion having a needle through hole formed at a center thereof in a circular plate shape, and a connection guide portion mounted on an outer surface of the supporting portion at an interval and having an inclined surface formed at an end thereof.

The moving guide portion may be configured with a rotation restriction portion protruding outward to limit a rotation operation and a moving guide inclined surface formed at one end of the rotation restriction portion.

A first spring positioned in a direction of the nozzle hole may be formed as a spring having a greater elasticity than a second spring positioned in a direction of the push member.

The push member and the connection member may be integrally formed.

The hair implanter with an automatically retracting needle may further include a disk including a needle through hole formed at a center thereof in a circular plate shape, and formed between the partition wall of the moving member and the first spring of the elastic member.

A hook may be mounted along the circumference of the mounting portion.

The other end of the case, in which the nozzle hole is formed, may be separately formed and is spirally coupled with the case to adjust a length of the other end.

A plurality of partitioning spaces may be formed inside the case, and the fixing member, the push member, the connection member, the moving member, the elastic member, and the hair transplantation needle may be mounted in the partitioning spaces.

An auxiliary case may be mounted on an outside of the case and a pressing unit configured to pressurize the push member may be mounted on an outside of the auxiliary case.

The auxiliary case may include a needle discharge hole formed at a center or one side thereof, and the pressing unit includes a driving motor provided with a screw, a pressing rod mounted on the screw and configured to pressurize the push member, a switch mounted on the auxiliary case, and a controller configured to control the driving motor.

A rotation motor may be mounted at a center of the auxiliary case.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
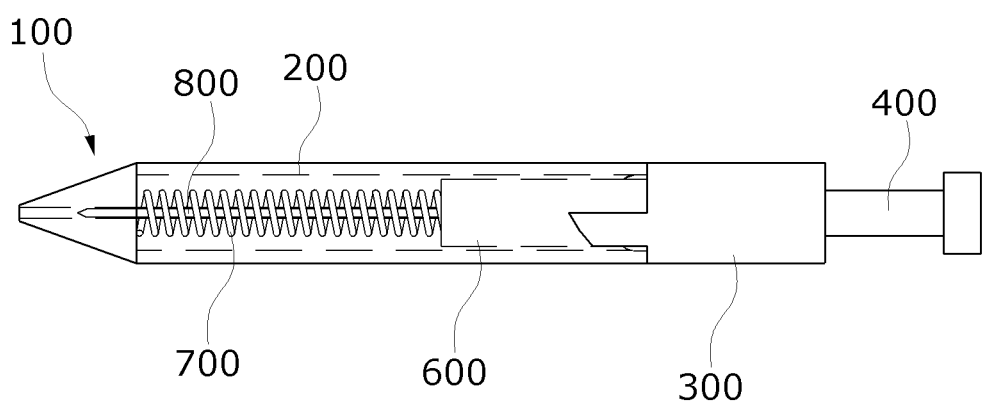
FIG. 1 is a side view illustrating a hair implanter with an automatically retracting needle according to the present disclosure.
Figure 2:
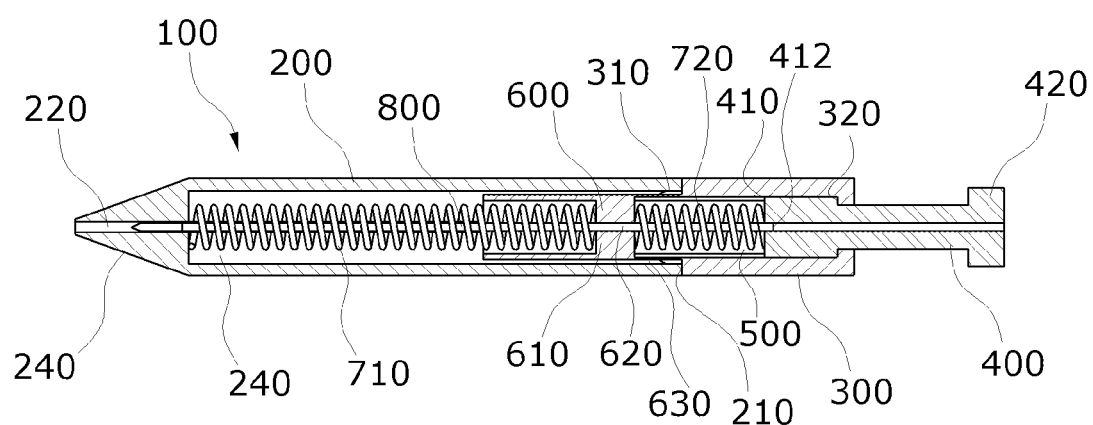
FIG. 2 is a side cross-sectional view illustrating the hair implanter with an automatically retracting needle according to the present disclosure.
Figure 3:
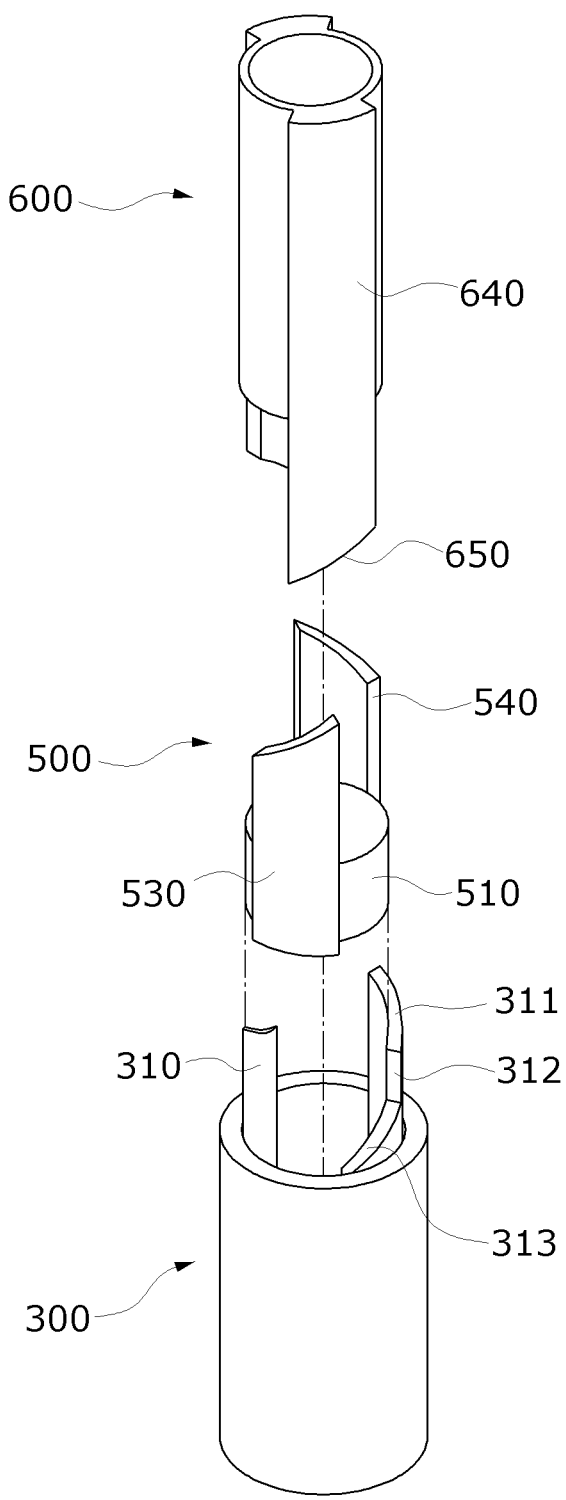
FIG. 3 is a perspective view illustrating a fixing member, a connection member, and a moving member constituting the hair implanter with an automatically retracting needle according to the present disclosure.
Figure 4:
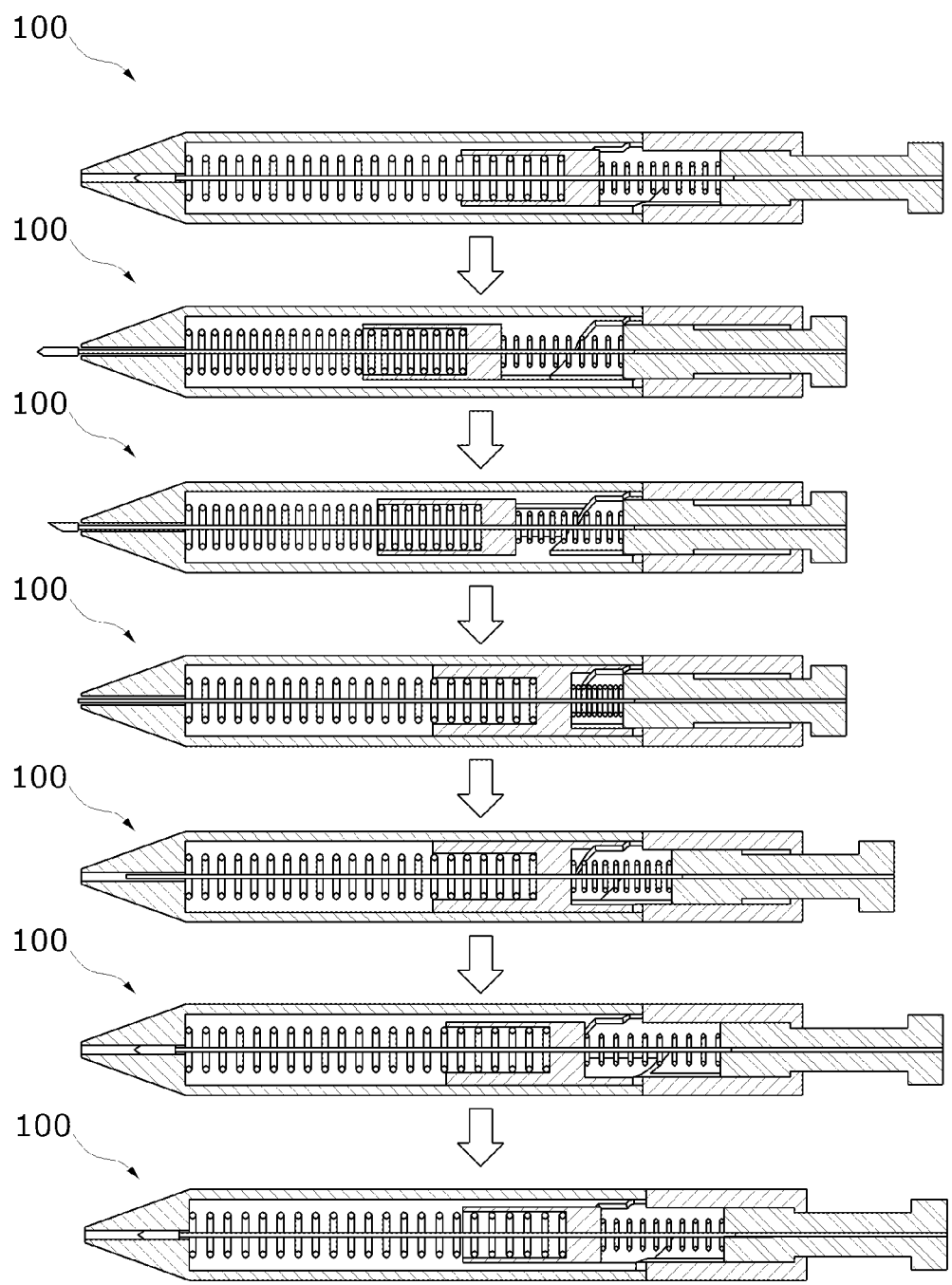
FIG. 4 is a side view illustrating an operating state of the hair implanter with an automatically retracting needle according to the present disclosure.

Hereinafter, exemplary embodiments of the present disclosure will be described in detail below with reference to the accompanying drawings. FIG. 1 is a side view illustrating a hair implanter with an automatically retracting needle according to the present disclosure, FIG. 2 is a side cross-sectional view illustrating the hair implanter with an automatically retracting needle according to the present disclosure, FIG. 3 is a perspective view illustrating a fixing member, a connection member, and a moving member constituting the hair implanter with an automatically retracting needle according to the present disclosure, FIGS. 5 to 10 are views illustrating another embodiment of a hair implanter with an automatically retracting needle according to the present disclosure.

A hair implanter with an automatically retracting needle 100 of the present disclosure includes a case 200, a fixing member 300, a push member 400, a connection member 500, a moving member 600, an elastic member 700, and a hair transplantation needle 800.

Here, the push member 400 and the connection member 500 may be integrally formed.

The case 200 has a hollow shape and is formed to have a certain diameter and length.

The case 200 has a cylindrical shape and has a mounting portion 210 formed at one end thereof, a nozzle hole 220 formed at the other end thereof, and an operating space 230 formed therein.

That is, in the case 200, the fixing member 300 configured to close or open the inside of the case 200 is mounted on the mounting portion 210, a passage configured to move the hair transplantation needle 800 and hair follicles is formed in the nozzle hole 220, and the operating space 230 provides a space required for the configuration for planting the hair follicles.

Here, the cross section of the case 200 is not limited to the illustrated drawings and may be formed in various shapes such as a quadrangular shape, a polygonal shape, or the like.

The outer surface 240 in which the nozzle hole 220 is formed is formed in a conical shape so that the hair follicle is smoothly positioned in the corresponding portion and the operation state may be visually confirmed easily.

The fixing member 300 is coupled to the mounting portion 210 of the case 200.

The fixing member 300 has a hollow shape, is coupled to the mounting portion 210 of the case 200, and has a fixing guide portion 310 formed at one end thereof and a step portion 320 formed at the other end thereof.

That is, the fixing member 300 is inserted into and coupled to the mounting portion 210 of the case 200, the fixing guide portion 310 is formed at one end of the fixing member 300 positioned in the operating space 230 of the case 200, and the step portion 320 is formed at the other end of the fixing member 300 positioned on the outside.

The fixing guide portion 310 includes a first inclined surface 311 positioned at an end thereof and formed to be inclined, a horizontal surface 312 formed at an end of the first inclined surface 311, and a second inclined surface 313 formed at an end of the horizontal surface 312, which are all disposed to be spaced apart from the fixing guide portion 310 along the circumference of an edge of the fixing member 300.

That is, the fixing guide portion 310 fixes the moving member 600 through the second inclined surface 313 while guiding the moving member 600 moving along the connection member 500 in a direction of the push member 400 through the first inclined surface 311.

Here, the first inclined surface 311 may be formed in multiple stages depending on environment, purpose, or the like.

Further, the step portion 320 supports one end of the push member 400 and prevents the push member 400 from being discharged to the outside.

The push member 400 is coupled to the fixing member 300 and operates forward and backward.

The push member 400 has one end 410 provided with a needle supporting groove 412 at the step portion 320 of the fixing member 300 and the other end 420 disposed on the outside, and operates forward and backward.

Here, the push member 400 may be formed in various shapes. In the present disclosure, the push member 400 has a cylindrical shape, and diameters of both ends 410 and 420 are formed to be greater than the inner diameter. Also, the needle supporting groove 412 is formed in the one end 410 so as to fix and support the hair transplantation needle 800.

The connection member 500 is disposed inside the fixing member 300 and operates in conjunction with the operation of the push member 400.

The connection member 500 includes a supporting portion 510 having a circular plate shape with a needle through hole 520 formed at a center thereof, and a connection guide portion 530 mounted on an outer surface of the supporting portion 510 at an interval and having an inclined surface 540 formed at an end thereof.

That is, the connection member 500 is disposed inside the fixing member 300, and one end thereof contacts the one end 410 of the push member 400 so that the connection member 500 operates in conjunction with the push member 400 to pressurize the elastic member 700 when the push member 400 is in operation.

Here, the inclined surface 540 formed on the connection guide portion 530 may be formed with the same inclination as the first inclined surface 311 of the fixing guide portion 310 constituting the fixing member 300 for smooth movement of the moving member 600.

That is, when the connection guide portion 530 is positioned outside the first inclined surface 311 of the fixing guide portion 310, the movement of the moving member 600 is limited. Also, when the connection guide portion 530 is moved beyond the first inclined surface 311 of the fixing guide portion 310, the moving member 600 is guided to the fixing guide portion 310 of the fixing member 300 using the inclined surface 540.

The moving member 600 is disposed in the operating space 230 of the case 200 and operates in conjunction with the push member 400 when the push member 400 is in operation.

Also, the moving member 600 has a certain length and diameter and has a partition wall 610 having a needle fixing hole 620, which is formed at the center therein, and a moving guide portion 630 formed at one end thereof.

Here, the moving member 600 is formed in various shapes, and in the present disclosure, for example, the moving member 600 is described as being formed in a cylindrical shape.

That is, the moving member 600 has a cylindrical shape having a certain diameter and length. Also, the partition wall 610 provided with the needle fixing hole 620 configured to fix the hair transplantation needle 800 is formed inside the moving member 600, and the moving guide portion 630 is formed at the one end of the moving member 600 so that the moving member 600 can move in the direction of the push member 400 when passing through the set section.

In addition, when the inclined surface 540 of the connection member 500 passes through the first inclined surface 311 of the fixing member 300 while the moving member 600 moves in the direction of the nozzle hole 220 together with the connection member 500 in operation of the push member 400, the moving guide portion 630 is fixed to the second inclined surface 313 while moving in the direction of the push member 400 through the inclined surface 540 of the connection member 500 and the first inclined surface 311 of the fixing guide portion 310.

The needle fixing hole 620 is formed to have a size capable of forcibly inserting the hair transplantation needle 800 therein.

Also, the moving guide portion 630 includes a rotation restriction portion 640, which protrudes outward to limit a rotation operation, and a moving guide inclined surface 650, which is formed at one end of the rotation restriction portion 640.

Here, the moving guide inclined surface 650 is formed so as to correspond to the inclined surface 540 of the connection member 500 or the first inclined surface 311 of the fixing guide portion 310.

The elastic member 700 may be mounted on one side or both sides of the moving member 600, and in the present disclosure, for example, the elastic member 700 is described as being mounted on both sides of the moving member 600.

Here, the elastic member 700 is formed as a configuration capable of performing an elastic function or a buffering function, and in the present disclosure, for example, the elastic member 700 is described as being configured with a spring.

That is, the elastic member 700 includes first and second springs 710 and 720 disposed on both sides of the moving member 600, moves the moving member 600 in the direction of the nozzle hole 220 when the push member 400 is being pressed, and moves the push member 400 and the moving member 600 to an original position thereof when the moving member 600 is moved in the pushing direction.

Here, although the first and second springs 710 and 720 may be formed of the same spring, the first spring 710 positioned in the direction of the nozzle hole 220 may be formed as a spring having a greater elasticity than the second spring 720 positioned in the direction of the push member 400 in order for the push member 400, the connection member 500, and the moving member 600 to operate quickly.

Also, the second spring 720 may be positioned between the push member 400 and the moving member 600 or may be mounted between the case 200 and the push member 400 to move the push member 400 backward.

The hair transplantation needle 800 is formed with a certain length and diameter.

Further, the hair transplantation needle 800 is fixed via the needle supporting groove 412 of the push member 400 and the needle fixing hole 620 of the moving member 600.

The hair transplantation needle 800 inserts the hair follicle into the scalp while operating in conjunction with the push member 400 when the push member 400 is in operation.

A hair implanter with an automatically retracting needle 100 according to the present disclosure may be configured as shown in FIGS. 5 to 11.

Figure 5:
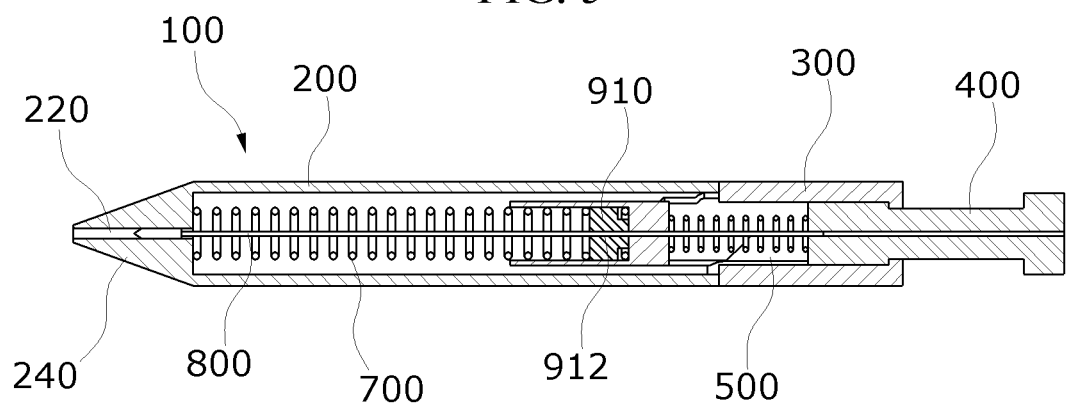
FIGS. 5 to 10 are views illustrating another embodiment of a hair implanter with an automatically retracting needle according to the present disclosure.

A hair implanter with an automatically retracting needle 100 shown in FIG. 5 is an example in which a disk 910 is further included between the moving member 600 and the elastic member 700.

That is, the disk 910 having a needle through hole 912 formed in a circular plate shape at a center thereof is mounted between the partition wall 610 of the moving member 600 and the first spring 710 of the elastic member 700 to reduce rotational friction when the hair implanter with an automatically retracting needle 100 is in operation.

Figure 6:
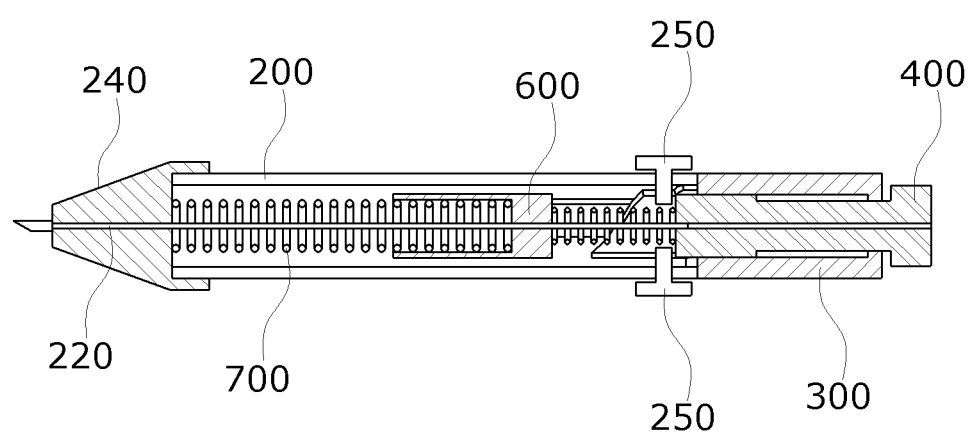

A hair implanter with an automatically retracting needle 100 shown in FIG. 6 is an example in which a hook 250 is mounted along the circumference of the mounting portion 210 of the case 200.

That is, the "T" shaped hook 250 is mounted along the circumference of the mounting portion 210 so that the case 200 adjusts a moving distance of the push member 400.

Also, FIG. 6 is an example in which the other end of the case 200, in which the nozzle hole 220 is formed, is separate from the case 200.

That is, the case 200 is configured to separate a portion in which the nozzle hole 220 is formed to adjust a protruding length of the hair transplantation needle 800.

Figure 7:
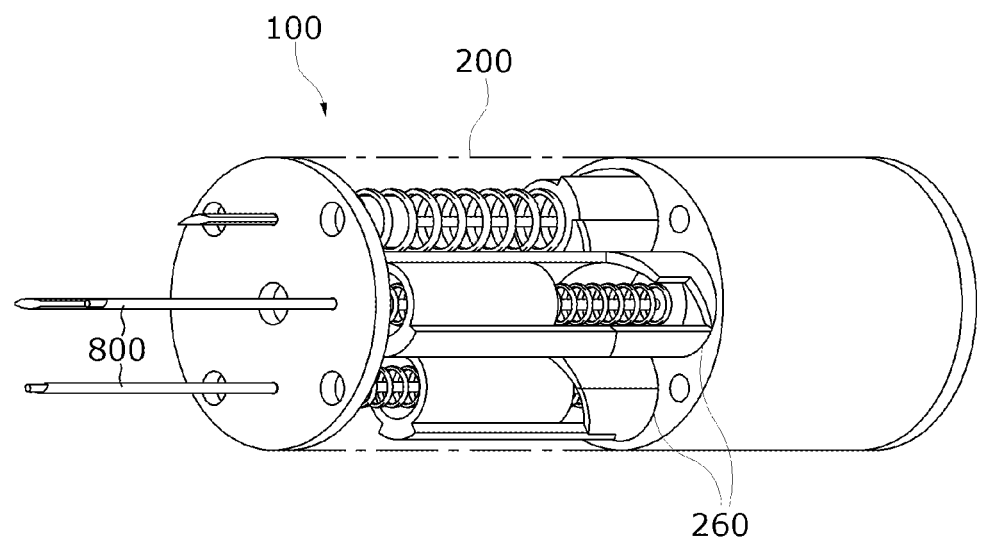
Figure 8:
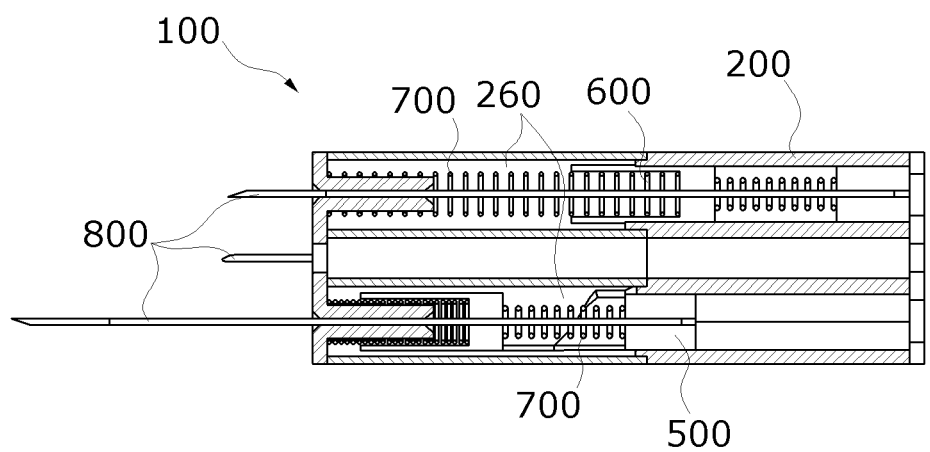

A hair implanter with an automatically retracting needle 100 shown in FIGS. 7 and 8 is an example in which a plurality of partitioning spaces 260 are formed inside the case 200, and the fixing member 300, the push member 400, the connection member 500, the moving member 600, the elastic member 700, and the hair transplantation needle 800 are mounted in the partitioning spaces 260.

That is, a plurality numbers of the hair implanter with an automatically retracting needle 100 are formed so that hair transplantation work may be continuously performed.

Figure 9:
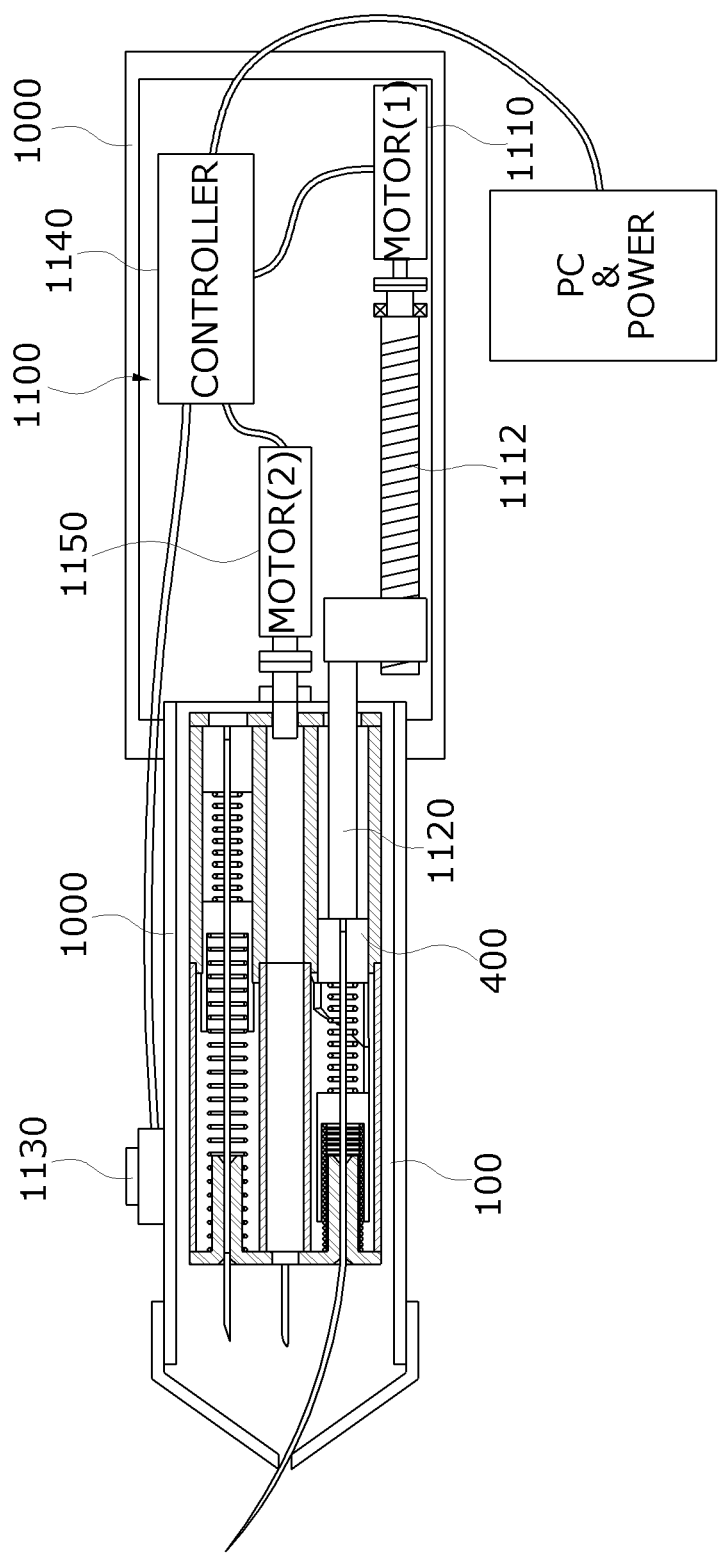
Figure 10:
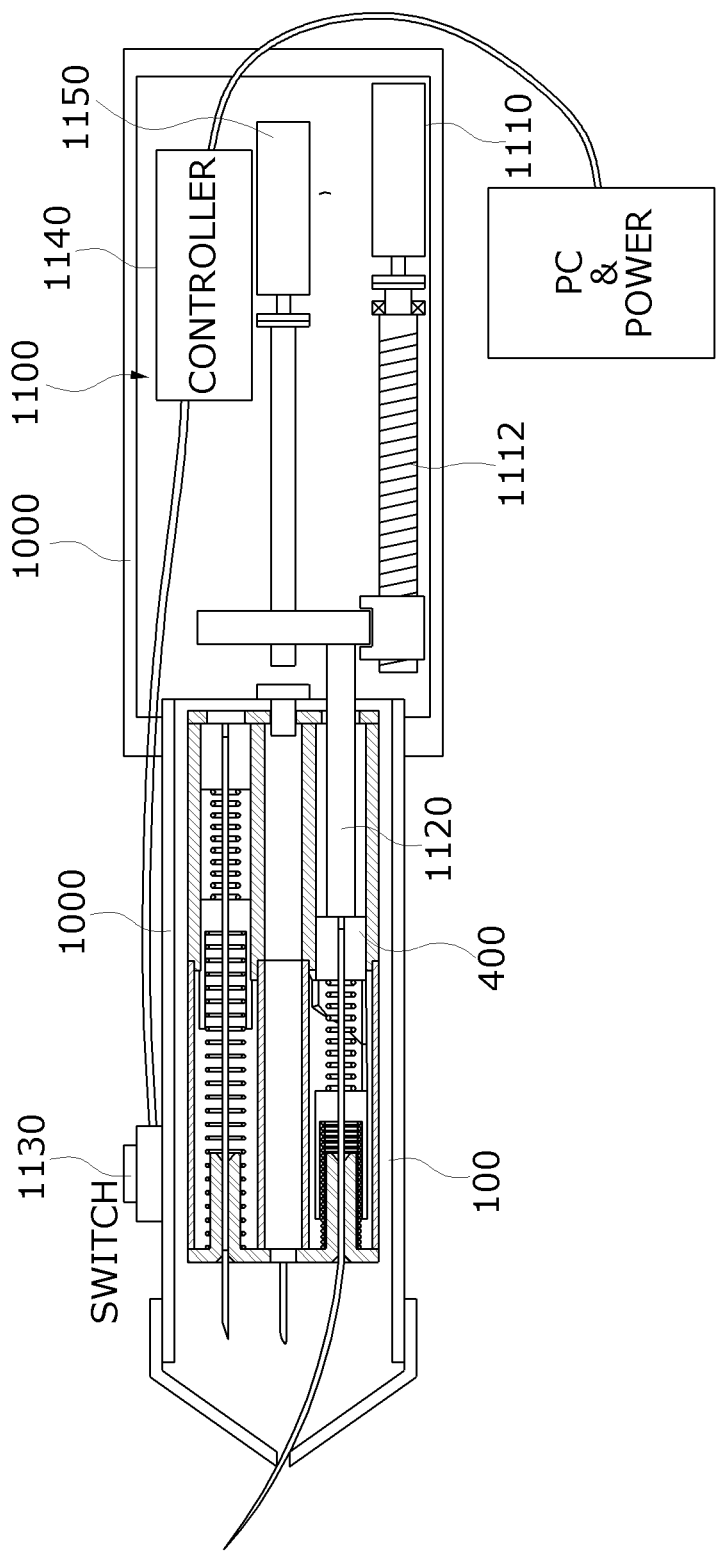
Figure 11:
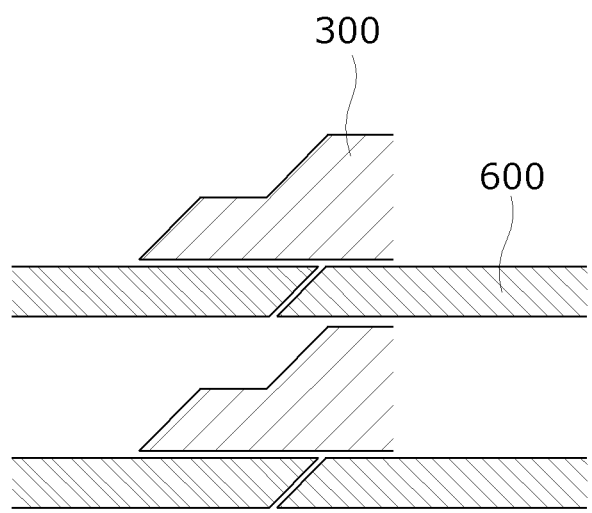
FIGS. 11 and 12 are view illustrating embodiments of an inclined surface of a fixing member constituting a hair implanter with an automatically retracting needle according to the present disclosure.
Figure 12:
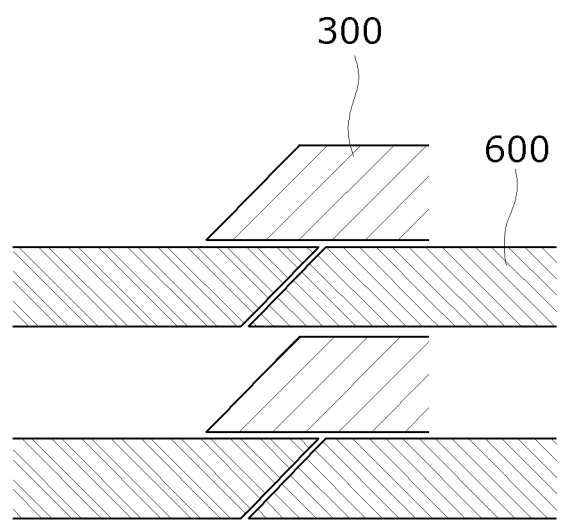

A hair implanter with an automatically retracting needle 100 shown in FIGS. 9 and 10 is an example in which an auxiliary case 1000 is mounted on the outside of the case 200 and a pressing unit 1100 configured to pressurize the push member 400 is mounted on the outside of the auxiliary case 1000.

Here, the auxiliary case 1000 may have a needle discharge hole 1010 formed at a center or one side thereof.

The pressing unit 1100 includes a driving motor 1110 provided with a screw 1112, a pressing rod 1120 mounted on the screw 1112 and configured to pressurize the push member 400, a switch 1130 mounted on the auxiliary case 1000, and a controller 1140 configured to control the driving motor 1110.

That is, the needle discharge hole 1010 is formed at a center of the auxiliary case 1000, and when the driving motor 1110 and the pressing rod 1120 constituting the pressing unit 1100 are in operation, the hair transplantation needle 800 is bent and discharged.

Here, the driving motor 1110 rotates through a rotation motor 1150 disposed at a center of the auxiliary case 1000 to discharge the hair transplantation needle 800 to the outside.

Further, FIGS. 9 and 10 show an example in which the pressing unit 1100 includes the driving motor 1110 provided with the screw 1112, the pressing rod 1120 mounted on the screw 1112 and configured to pressurize the push member 400, the switch 1130 mounted on the auxiliary case 1000, the controller 1140 configured to control the driving motor 1110, and the rotation motor 1150 configured to rotate the auxiliary case 1000.

That is, the pressing unit 1100 rotates the auxiliary case 1000 and the case 200 according to the operation of the rotation motor 1150 and then linearly discharges the hair transplantation needle 800 when the driving motor 1110 and the pressing rod 1120 constituting the pressing unit 1100 are in operation.

An embodiment of the hair implanter with an automatically retracting needle constituted as described above will be described as follows.

First, a case 200 which has a cylindrical shape and has a mounting portion 210 formed at one end thereof, a nozzle hole 220 formed at the other end thereof, and an operating space 230 therein is formed.

Next, a moving member 600 is inserted into the operating space 230 of the case 200. Here, the moving member 600 includes a partition wall 610, which is provided with a needle fixing hole 620 having a cylindrical shape with a certain diameter and length and formed at the center of the inner portion of the moving member 600, and a moving guide portion 630 including a rotation restriction portion 640 and a moving guide inclined surface 650, which is formed at one end of the rotation restriction portion 640, and formed at one end of the moving member 600.

Here, an elastic member 700 in which first and second springs 710 and 720 are disposed on both sides of the partition wall 610 constituting the moving member 600 is mounted.

Next, a fixing member 300 having a hollow shape, coupled to the mounting portion 210 of the case 200, and having a fixing guide portion 310 at one end thereof and a step portion 320 at the other end thereof is formed.

Next, a push member 400 having one end 410 provided with a needle supporting groove 412 at the step portion 320 of the fixing member 300 in a cylindrical shape and the other end 420 disposed on the outside is mounted.

Next, a connection member 500 is mounted inside the fixing member 300. Here the connection member 500 includes a supporting portion 510 having a circular plate shape and a needle through hole 520 formed at the center thereof, and a connection guide portion 530 mounted on an outer surface of the supporting portion 510 at an interval and having an inclined surface 540 formed at an end thereof.

Afterward, the fixing member 300 provided with the push member 400 and the connection member 500 is mounted on the mounting portion 210 of the case 200, and then a hair transplantation needle 800 having a certain diameter and length is mounted in the needle supporting groove 412 of the push member 400, and the needle fixing hole 620 of the moving member 600 to complete the assembly of the hair implanter with an automatically retracting needle 100.

The assembly procedure of the hair implanter with an automatically retracting needle may be performed differently from the above description.

An embodiment of the hair implanter with an automatically retracting needle constituted as described above will be described as follows.

A hair follicle is inserted into the nozzle hole 220 of the case 200 and an end of the hair follicle is positioned at an end of the hair transplantation needle 800. Thereafter, an end of the outer surface 240 of the case 200 is brought into close contact with the scalp, and the push member 400 is pressed.

The hair transplantation needle 800 is inserted through the scalp, and the first spring 710 of the elastic member 700 is compressed.

In addition, when the moving guide portion 630 of the moving member 600 passes through the first inclined surface 311 of the fixing member 300, the moving member 600 moves to the inclined surface 540 of the connection member 500 and the first inclined surface 311 of the fixing member 300 while the moving guide inclined surface 650 of the moving guide portion 630 is rotated.

The moving member 600 stops the rotation and moving in the direction of the push member 400 by the rotation restriction portion 640 and the horizontal surface 312 while the moving guide inclined surface 650 of the moving guide portion 630 reaches the horizontal surface 312 via the first inclined surface 311.

Here, the hair transplantation needle 800 operates in conjunction with the above-described operation to prevent the needle inserted into a scalp from pulling out of the scalp and prevent the hair follicles from coming out of the scalp.

The connection member 500 and the push member 400 are moved in the direction of the push member 400 by the second spring 720 of the elastic member 700 when the outer surface 240 of the case 200 is separated from the scalp and the applied pressure transmitted to the push member 400 is removed.

In addition, when the applied pressure transmitted to the push member 400 is completely removed, the push member 400 and the connection member 500 return to original positions thereof. Also, the moving member 600 moves in the direction of the nozzle hole 220 and returns to the original position thereof along the first inclined surface 311 and inclined surface 540 when the moving guide portion 630 reaches the first inclined surface 311 of the fixing member 300.

According to the present disclosure, a height of the hair follicle can be easily matched to a height of the scalp in the hair transplantation process, and a hair implanter can insert the hair follicle into the scalp at an appropriate position with a single operator action of pushing a push member.

In addition, a hair transplantation work can be continuously performed using such a mechanism.

While the present disclosure has been particularly described with reference to exemplary embodiments, it will be understood by those skilled in the art that various changes in form and details may be made without departing from the spirit and scope of the present disclosure.

Therefore, the exemplary embodiments should be considered in a descriptive sense only and not for purposes of limitation. The scope of the disclosure is defined not by the detailed description of the disclosure but by the appended claims, and encompasses all modifications and equivalents that fall within the scope of the appended claims.

What is claimed is:

1. A hair implanter with an automatically retracting needle, the hair implanter comprising:
    a case which has a hollow shape and includes a mounting portion formed at one end thereof and a nozzle hole formed at the other end thereof;
    a fixing member which has a hollow shape, is coupled to the mounting portion of the case, and includes a fixing guide portion formed at one end thereof and a step portion formed at the other end thereof;
    a push member which operates forward and backward and includes a first end provided with a needle supporting groove and disposed on the step portion of the fixing member and a second end;
    a connection member disposed inside the fixing member and operating in conjunction with the operation of the push member and having an inclined surface at one end;
    a moving member which is disposed inside the case, operates in conjunction with the operation of the push member, and includes a partition wall provided with a needle fixing hole formed at a center thereof and a moving guide portion formed at one end thereof;
    an elastic member including first and second springs disposed on both sides of the partition wall of the moving member, and configured to move the moving member in a direction of the nozzle hole when the push member is pressed and to move the push member and the moving member to an original position thereof after the push member is pressed; and
    a hair transplantation needle which is fixed by the needle supporting groove of the push member and the needle fixing hole of the moving member,
    wherein the fixing guide portion of the fixing member comprises a first inclined surface facing the moving member, a horizontal surface formed at an end of the first inclined surface, and a second inclined surface formed at an end of the horizontal surface,
    wherein the first and second inclined surfaces and the horizontal surface are disposed along a circumference of an edge of the fixing member and coupled to the fixing member, and
    wherein the second inclined surface of the fixing member and the inclined surface of the connection member are inclined at the same angle, and the moving guide portion has an inclined surface that engages with the first inclined surface of the fixing member and the inclined surface of the connection member.

2. The hair implanter of claim 1, wherein an outer surface of the other end of the case, in which the nozzle hole is formed, is formed in a conical shape.

3. The hair implanter of claim 1, wherein the first inclined surface is formed in multiple stages.

4. The hair implanter of claim 1, wherein the connection member comprises a supporting portion having a needle through hole formed at a center thereof in a circular plate shape, and a connection guide portion mounted on an outer surface of the supporting portion at an interval.

5. The hair implanter of claim 1, wherein the moving guide portion is configured with a rotation restriction portion protruding outward to limit a rotation operation and the moving guide inclined surface is formed at one end of the rotation restriction portion.

6. The hair implanter of claim 1, wherein the first spring is positioned in a direction of the nozzle hole and has a greater elasticity than the second spring, which is positioned in a direction of the push member.

7. The hair implanter of claim 1, wherein the push member and the connection member are integrally formed.

8. The hair implanter of claim 1, further comprising a disk including a needle through hole formed at a center thereof in a circular plate shape, and formed between the partition wall of the moving member and the first spring of the elastic member.

9. The hair implanter of claim 1, wherein a hook is mounted along the circumference of the mounting portion.

10. The hair implanter of claim 1, wherein the other end of the case, in which the nozzle hole is formed, is separately formed and is spirally coupled with the case to adjust a length of the other end.

11. The hair implanter of claim 1, wherein a plurality of partitioning spaces are formed inside the case, and the fixing member, the push member, the connection member, the moving member, the elastic member, and the hair transplantation needle are mounted in the partitioning spaces.

12. The hair implanter of claim 11, wherein an auxiliary case is mounted on an outside of the case and a pressing unit configured to pressurize the push member is mounted on an outside of the auxiliary case.

13. The hair implanter of claim 12, wherein the auxiliary case comprises a needle discharge hole formed at a center or one side thereof, and the pressing unit includes a driving motor provided with a screw, a pressing rod mounted on the screw and configured to pressurize the push member, a switch mounted on the auxiliary case, and a controller configured to control the driving motor.

14. The hair implanter of claim 13, wherein a rotation motor is mounted at a center of the auxiliary case.

\* \* \* \* \*